United States Patent
Gordon et al.

(10) Patent No.: US 7,267,008 B2
(45) Date of Patent: Sep. 11, 2007

(54) DRIVE, TRANSMIT & RECEIVE CIRCUIT FOR STRUCTURAL HEALTH MONITORING SYSTEMS

(75) Inventors: Grant A. Gordon, Peoria, AZ (US); Nicholas Wilt, Glendale, AZ (US)

(73) Assignee: Honeywell International, Inc., Morristown, NJ (US)

( * ) Notice: Subject to any disclaimer, the term of this patent is extended or adjusted under 35 U.S.C. 154(b) by 281 days.

(21) Appl. No.: 11/046,259

(22) Filed: Jan. 28, 2005

(65) Prior Publication Data

US 2006/0169046 A1    Aug. 3, 2006

(51) Int. Cl.
G01N 29/12    (2006.01)
G01N 29/14    (2006.01)
G01N 1/00    (2006.01)

(52) U.S. Cl. .................................................. 73/587
(58) Field of Classification Search ................ 73/643, 73/587, 594; 385/12–13; 250/227.18; 356/477, 356/782
See application file for complete search history.

(56) References Cited

U.S. PATENT DOCUMENTS

| | | | |
|---|---|---|---|
| 5,195,046 A * | 3/1993 | Gerardi et al. ............. 702/35 |
| 5,293,555 A * | 3/1994 | Anthony ..................... 702/36 |
| 5,440,300 A * | 8/1995 | Spillman, Jr. ........... 340/10.34 |
| 5,798,458 A * | 8/1998 | Monroe ....................... 73/587 |
| 6,074,346 A | 6/2000 | Oppelt |
| 6,083,164 A | 7/2000 | Oppelt et al. |
| 6,161,434 A * | 12/2000 | Fink et al. .................... 73/587 |
| 6,269,052 B1 | 7/2001 | Oppelt |
| 6,370,964 B1 * | 4/2002 | Chang et al. .......... 73/862.046 |
| 6,399,939 B1 * | 6/2002 | Sundaresan et al. ..... 250/231.1 |
| 7,117,742 B2 * | 10/2006 | Kim ............................. 73/587 |

* cited by examiner

Primary Examiner—Hezron Williams
Assistant Examiner—Rose M. Miller
(74) Attorney, Agent, or Firm—Ingrassia Fisher & Lorenz

(57) ABSTRACT

A transducer for use in a structural health monitoring system includes a single transducer element. The transducer includes a transmit assembly coupled to the single transducer element. This assembly is configured to produce a multi-cycle square wave drive signal for stimulating the transducer. Additionally, a transmit/receive switch coupled to the single transducer element is provided. This assembly is configured to isolate the drive signal from the receive assembly used to sense the electrical signal generated from any received elastic waves.

26 Claims, 6 Drawing Sheets

DRIVE, TRANSMIT & RECEIVE CIRCUIT FOR STRUCTURAL HEALTH MONITORING SYSTEMS

TECHNICAL FIELD OF THE INVENTION

This invention relates to the field of structural health monitoring and, more particularly, to the use of a simple, inexpensive circuit to drive, transmit and receive ultrasonic signals for each single element ultrasonic transducer of a structural health monitoring system.

BACKGROUND OF THE INVENTION

Nondestructive testing is a procedure for determining the quality or characteristics of a structure without permanently altering the structure's properties. Examples include ultrasonic and radiographic inspection. In the avionics field, nondestructive evaluations of airplane components are performed to insure the structural integrity of the airplane.

In ultrasonic testing, ultrasonic transducers are used. Ultrasonic transducers convert electrical signals into mechanical vibrations in a test material and mechanical vibrations into electrical signals. Typically, ultrasonic transducers convert electrical signals into mechanical vibrations that propagate waves in the material to be tested via elastic deformations (the propagated waves are also known as elastic waves). The propagated waves interact with various features within the test material, such as flaws or defects. The ultrasonic transducers can also receive transmitted and reflected waves and convert the received waves into electrical signals. The received electrical signals can then be analyzed to determine if there are flaws or defects in the test material.

While different designs exist for ultrasonic transducers, a typical ultrasonic transducer utilizes a piezoelectric transducer. Piezoelectric transducers produce mechanical vibrations via the application of an electrical signal to an appropriate piezoelectric crystal or ceramic. In ultrasonic testing, the amount of electricity used to send a pulse is generally much greater than the signal received by the transducer. One drawback to ultrasonic testing is that when sending a pulse, unless the receiver is isolated from the transmitter, the voltage used to generate the pulse may saturate or overwhelm the receiver electronics, decreasing the recorded fidelity of the received echo signals.

Various solutions have been developed in structural health monitoring systems employing piezoelectric transducers to alleviate this problem. One approach is to employ multiple piezoelectric elements in a single ultrasonic transducer. For example, a transducer may include a piezoelectric ceramic element for transmitting the ultrasonic pulses coupled to transmitter electronics and a separate piezoelectric ceramic element for receiving echoes coupled to the appropriate receiver electronics. In other approaches, the transmitter does not act as a receiver, and any elastic energy is sensed only by other transducers within the structural health monitoring system.

One drawback is that providing separate transmit and receive elements increases the complexity, cost, weight and size of an ultrasonic transducer. In the area of medical ultrasound, single element transducers are used with a switch to isolate the receiver circuitry from the transducer drive signal. However, structural health monitoring (SHM) systems differ from medical ultrasound systems in several ways. First, the SHM systems generally operate at much lower frequencies than medical ultrasonic probes. In addition, a structural health monitoring system often uses a much larger number of sensors distributed and attached over a much larger area. The large number of sensors along with the finite power resources and weight limitations of an avionics environment favor the use of lower voltage drive signals along with simple transducers and transmit/receive circuitry.

SUMMARY OF THE INVENTION

In one embodiment of the present invention a transducer having a single transducer element for use in a structural health monitoring system is disclosed. The transducer comprises a transmit assembly coupled to the single transducer element. This assembly is configured to produce a multi-cycle square wave drive signal for stimulating the transducer. Additionally, a transmit/receive switch coupled to the single transducer element is provided. This assembly is configured to isolate the drive signal from the receive assembly used to sense the electrical signal generated from any received elastic waves.

In another embodiment, a structural health monitoring system for use as an embedded monitoring system is disclosed. The system includes transducers having single transducer elements for use in a structural health monitoring system. Each transducer is mounted to the structure to be monitored. The transducer comprises a transmit assembly coupled to the single transducer element. This assembly is configured to produce a multi-cycle square wave drive signal for stimulating the transducer. Also, the transducer comprises a transmit/receive assembly coupled to the single transducer element. This assembly is configured to isolate the drive signal from the receive assembly used to sense the electrical signal generated from any received elastic waves. The system further comprises a processor coupled to the transducer and configured to evaluate data generated by the transducer.

BRIEF DESCRIPTION OF THE INVENTION

The present invention will hereinafter be described in conjunction with the following drawing figures, wherein like numerals denote like elements, and:

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description. While the invention is disclosed in an avionics embodiment, the teachings of the present invention are applicable to many different fields of endeavor.

In one embodiment of the present invention a method for using a single element transducer in a structural health monitoring system is disclosed. The transducer comprises a receive assembly and a transmit assembly, which are both coupled to a transmit/receive switch. The transmit/receive switch blocks high voltage signals from reaching the receiving electronics while the transducer is being driven yet allows the receiver to sense the low voltages generated by detection of the return echoes. For the purposes of this disclosure we will represent the high voltage blocking condition as an open switch, and the low voltage pass through condition as a closed switch.

Figure 1:
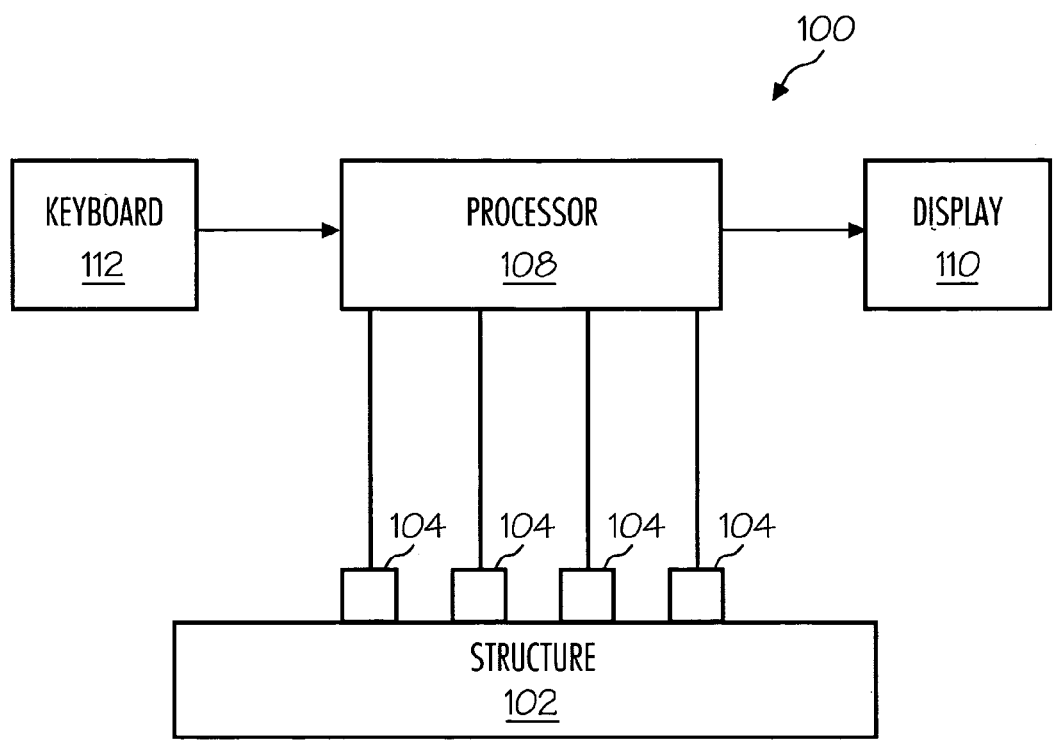
FIG. 1 is a block diagram of an exemplary embodiment of a structural monitoring system in accordance with the teachings of the present invention.

FIG. 1 illustrates an exemplary structural health management system 100 in accordance with the teachings of the present invention. Structural health management system 100 includes a plurality of sensors 104 mounted to a structure 102 to be tested. The sensors 104 are provided as an input to at least one structural health monitoring processor 108. Various inputs and outputs can be provided to structural health monitoring processor 108. For example, processor 108 can be coupled to various input/output devices including a display 110, a keyboard 112 and the like.

Processor 108 can be any device that can receive data from the sensors 104 to find or to help find flaws or defects in the structure 102. Processor 108 can be a commercial off the shelf processor and can include any components necessary to allow processor 108 to process the data, including memory, storage and the like. Various testing algorithms can also be run on processor 108. Processor 108 can couple to input/output devices such as a CRT or LCD display 110 that display information to a user and keyboards 112 and similar devices that allow for user input.

Structure 102 can be any one of numerous types of material of interest to be tested. In one embodiment, structure 102 is a composite material used for the skin of an aircraft.

Sensors 104 can be ultrasonic transducers that convert electrical signals into mechanical vibrations and mechanical vibrations into electrical signals. As discussed previously, sensors 104 can operate as transmitters by converting electricity into mechanical vibrations so that elastic waves propagate in the structure 102 to which the sensors 104 are coupled. These propagated waves interact with various features within the structure 102 such as flaws or defects. The sensors 104 can also operate as a receiver by receiving transmitted and reflected waves and converting the mechanical vibrations caused by these waves into electrical signals. These electrical signals can then be analyzed, such as at processor 108, to determine if there are any flaws or defects in the structure 102.

The amount of time it takes for a wave to travel between two sensed locations is known as the time-of-flight. In addition to time-of-flight, signal amplitude, signal energy (as represented by the area under the rectified voltage curve) and other signal features can be used in models to predict the underlying damage state of the area traversed by the propagated elastic waves. Various features within the structure 102, such as fatigue cracks or other structural flaws, can be identified and located based on these values obtained from data collected by the sensors 104.

While many different designs for sensors 104 exist, in one embodiment of the present invention, sensor 104 is a single element piezoelectric transducer. Single element piezoelectric transducers use the same piezoelectric crystal or ceramic to produce and receive mechanical vibrations. Piezoelectric transducers produce mechanical vibrations when an electric signal is applied and generate electrical signals when receiving mechanical vibrations. Typically, piezoelectric transducer uses piezoelectric ceramics that can be engineered to produce different wave modes.

Different types of waves induced by piezoelectric transducers can be used in nondestructive testing. In an embodiment of the present invention, the sensors 104 produce Lamb waves in structure 102. Lamb waves propagate throughout the entire thickness of plate-like structures, such as the composite material used for the skin of an aircraft. Lamb waves are a form of guided elastic waves distinct from the bulk waves used in traditional ultrasonic approaches. Lamb waves traverse along the plate-like structure while exciting material throughout the plate's thickness. As a consequence, the use of Lamb waves allows distributed sensor schemes to examine the composite plate-like structure over a given area without the need to scan the transducers over the area.

Figure 2:
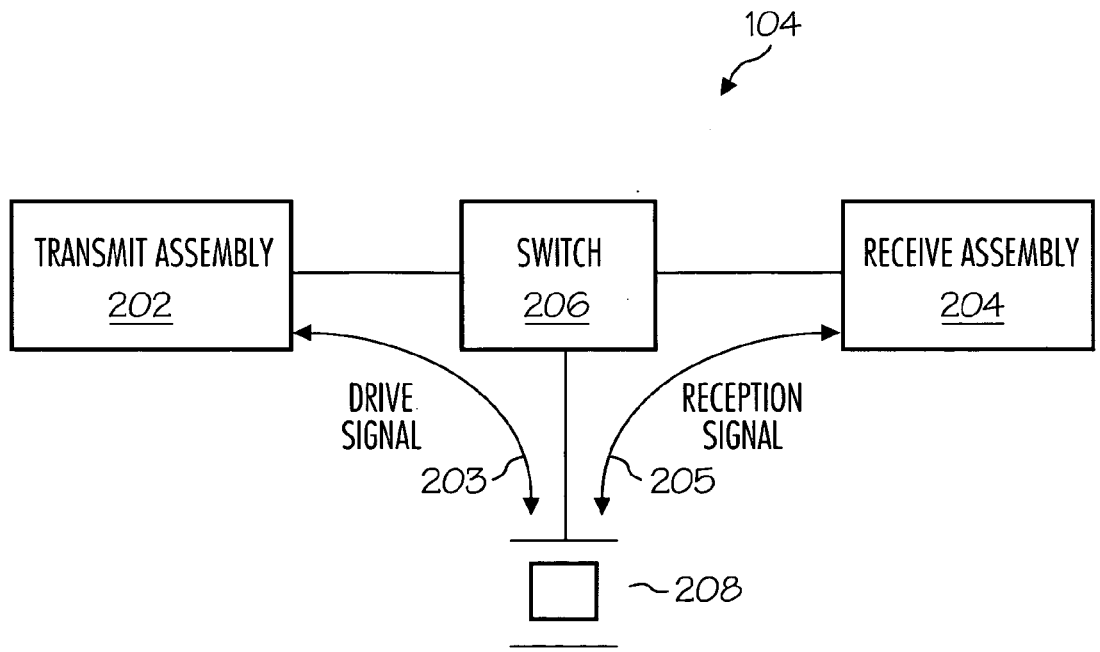
FIG. 2 is a block diagram of an exemplary ultrasonic transducer in accordance with the teachings of the present invention.
Figure 3:
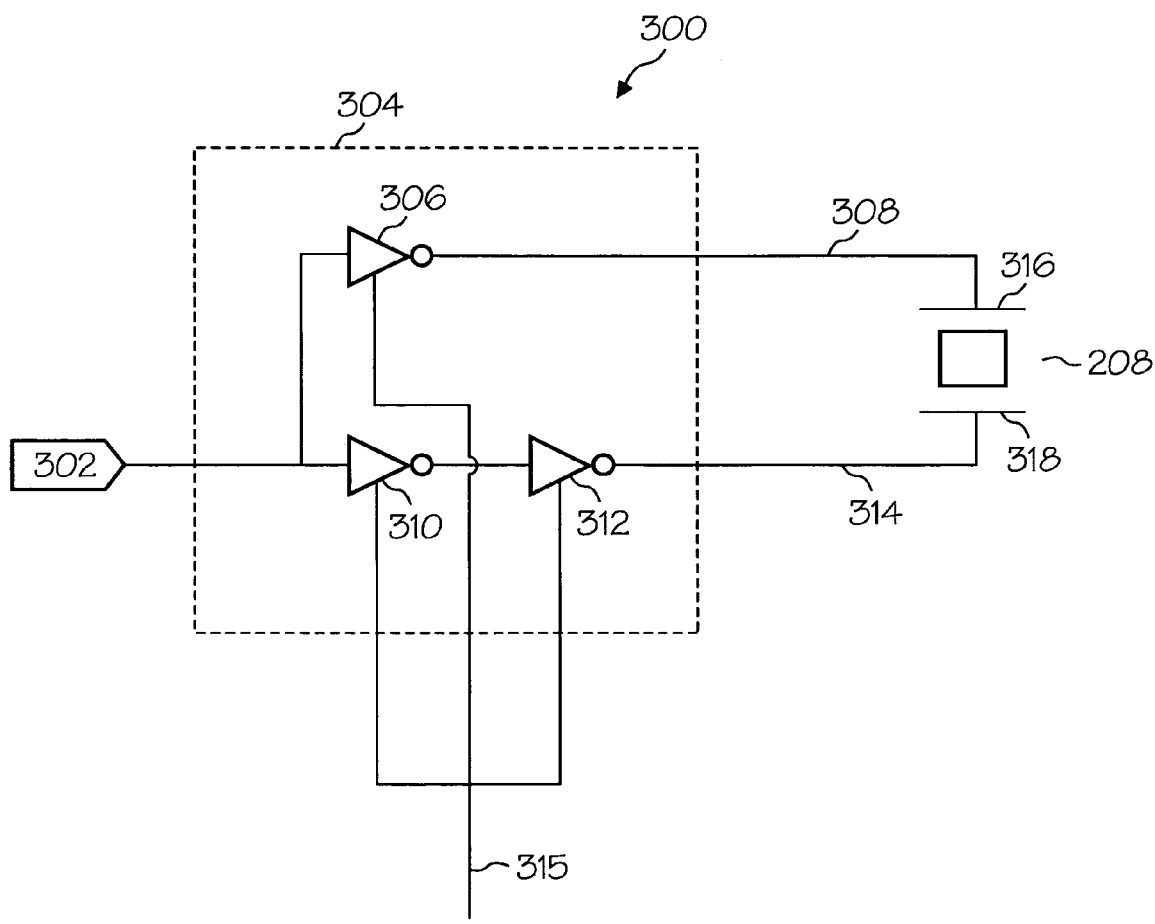
FIG. 3 is a block diagram of an exemplary drive signal supply for use in the present invention.

An exemplary sensor 104 is illustrated in FIGS. 2-3. Sensor 104 comprises a transmit assembly 202 coupled to a transducer element 208 and to a receive assembly 204 by a transmit/receive switch 206.

Transmit assembly 202 generates a transmission signal 203 for presentation to the transducer element 208. Transmit assembly 202 includes all necessary components to generate a signal that will be converted to a mechanical pulse by the transducer element 208. For example, transmit assembly can include a multi-cycle square wave generator, as seen in FIG. 3.

Receive assembly 204 receives a reception signal 205 from the transducer element 208 and performs any necessary processing of the reception signal 205. Receive assembly 204 comprises all components necessary to implement the receive assembly 204, including but not limited to any necessary amplifiers and filters.

Transducer element 208 converts electrical energy generated by the transmit assembly 202 into mechanical pulses and receives mechanical pulses from the material under test and converts these pulses to electrical signals for use by the receive assembly 204. In the present invention, the transducer element 208 comprises a single piezoelectric ceramic element.

The transmit/receive switch 206 prevents the receive assembly 204 from receiving high voltage when the transmit assembly 202 generates the voltage that forms the drive signal 203. In one embodiment, the transmit/receive switch 206 comprises a circuit that is forward biased when the transmit assembly 202 sensor 104 is not producing a transmission signal 203. When transmit assembly 202 starts to generate the drive signal 203, the circuit becomes reverse biased as the voltage level rises and the transmit/receive switch 206 behaves like an open circuit, isolating the receive assembly 204 from the large voltage of the transmission signal.

FIG. 3 illustrates an exemplary pulse generator 300 for use as part of the transmit assembly 202. Pulse generator 300, in one embodiment, is a multi-cycle square wave generator. Pulse generator 300 includes a unipolar signal source 302 coupled to a driver 304. Driver 304 comprises a first inverter 306 coupled to a first circuit leg 308 and a second inverter 310 coupled to a third inverter 312, both of which are coupled to a second circuit leg 314. First circuit leg and second circuit leg 314 are coupled to either side of transducer element 208.

The unipolar signal generating source 302 generates a voltage waveform of the appropriate shape. In one embodiment, a square wave varying from 0 to 5 volts is provided to the driver 304. Driver 304 can be coupled to control lines 315 that determine when the driver 304 receives the voltage waveform from the signal generating source to produce drive signals. For example, the processor 108 can generate control signals for control lines 315 to turn on and off the driver 304.

When the driver 304 is set to produce a drive signal, the driver 304 receives the unipolar voltage waveform from the signal-generating source 302. The voltage waveform is inverted by the first inverter 306 to form an inverted waveform and is inverted twice by inverters 310 and 312, resulting in an uninverted voltage waveform. The inverter wave is provided to a first side 316 of transducer element 208 and the uninverted waveform is provided to a second side 318 of transducer element 208. In an exemplary embodiment, the transducer element 208 has a floating ground. Thus, the transducer element sees alternating voltage steps at the first side 316 and then to the second side 318. In an exemplary embodiment where the signal generating source is a square wave of 0 to 5 volts, the net effect across the transducer element 208 is a multi-cycle square wave drive signal that alternates from −5 volts to 5 volts.

Figure 4:
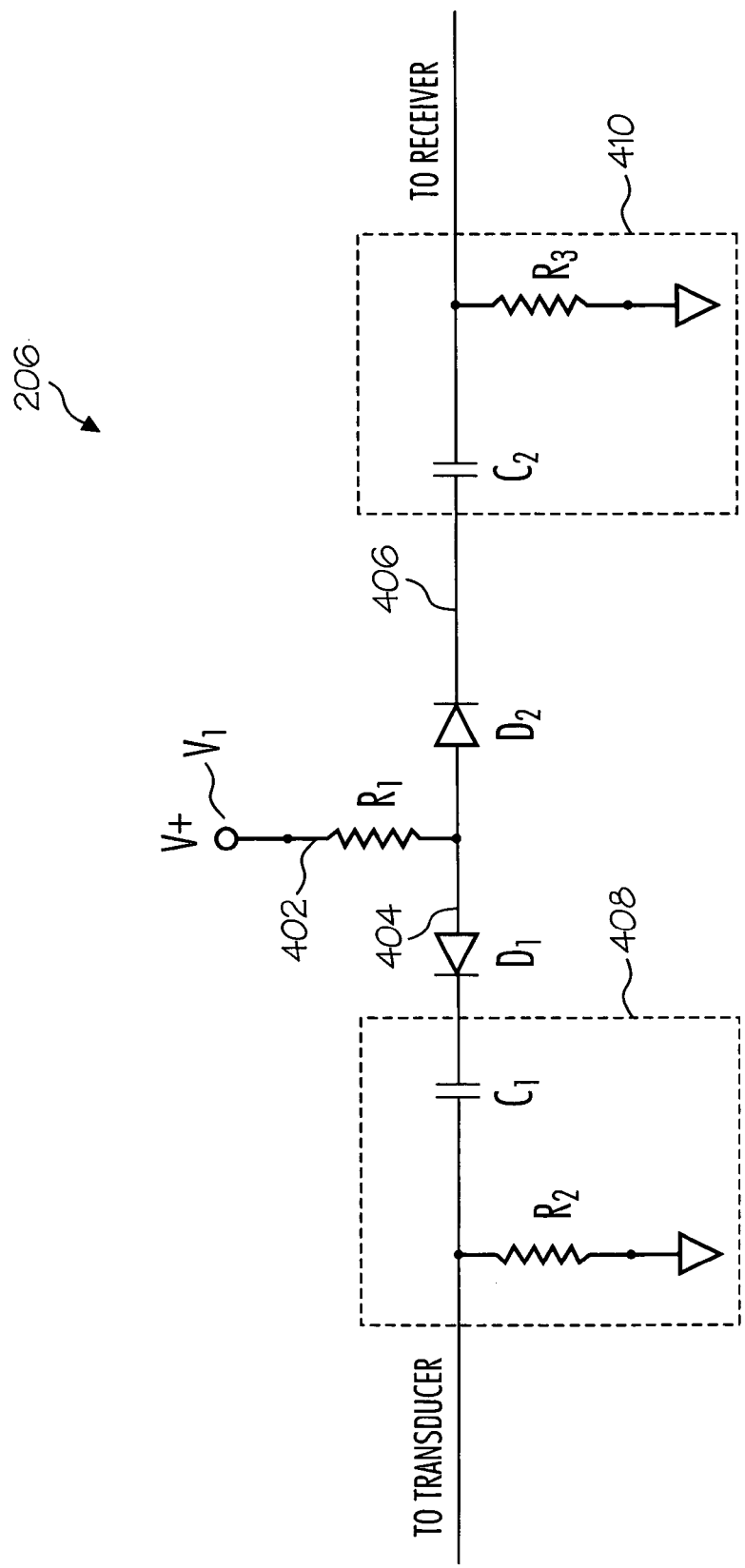
FIG. 4 illustrates an exemplary transmit/receive switch in accordance with the teachings of the present invention.

FIG. 4 illustrates an exemplary circuit 400 for use as the transmit/receive switch 206. A voltage source, $V_1$, located on a first circuit branch 402, supplies a bias voltage to diode, $D_1$, located on a second circuit branch 404 and diode, $D_2$, located on a third circuit branch 406. Second circuit branch 404 couples to the transmit assembly 202 and third circuit branch 406 couples to the receive assembly 204. A resistor, $R_1$, is provided on first circuit branch 402. Between $D_1$ and the transmit assembly 202 is a first R-C network 408 comprising a capacitor, $C_1$, and a resistor, $R_2$. Between $D_2$ and receive assembly 204 is a second R-C network 410 comprising a capacitor, $C_2$, and a resistor, $R_3$.

Figure 5:
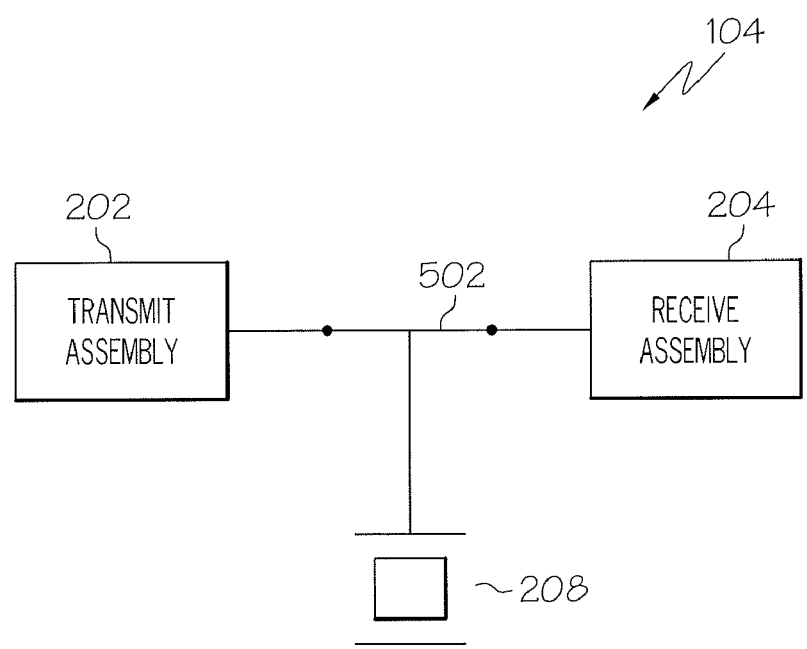
FIG. 5 is a block diagram of the exemplary embodiment of FIG. 1 with the transmit/receive switch acting like a closed mechanical switch.

In operation, voltage, $V_1$, provides sufficient voltage to diodes, $D_1$ and $D_2$ to forward bias $D_1$ and $D_2$. In the exemplary embodiment of FIG. 4, first R-C network 408 and second R-C network 410 act as high pass filters. The exact design of the R-C networks is not essential to the invention and, as is known in the art, can be interchanged with any number of resistors, capacitors and inductor combinations. The block diagram of FIG. 2 when $D_1$ and $D_2$ are forward biased can be seen in FIG. 5 where the transmit/receive switch 206 behaves like a conductor, and can be illustrated as a wire 502.

Figure 6:
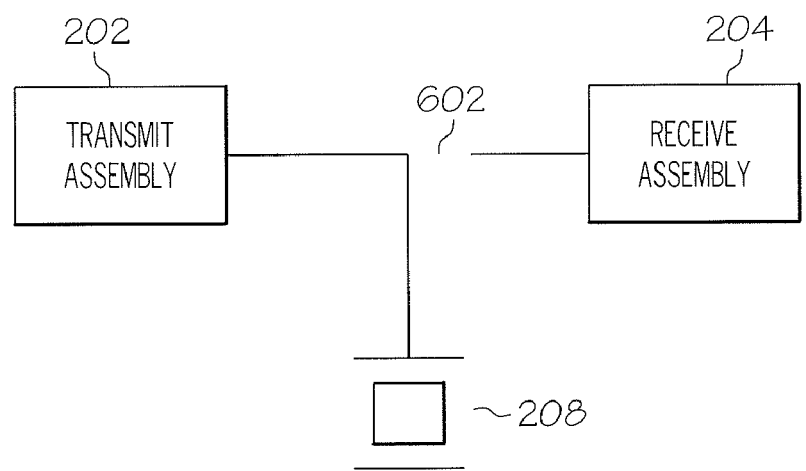
FIG. 6 is a block diagram of the exemplary embodiment of FIG. 1 with the transmit/receive switch acting like an open mechanical switch.

When the transducer is used to generate a pulse, the transmit assembly 202 generates a drive signal that will be applied to the transducer element 208. In one embodiment, the drive signal is a 0.1 ms triangular pulse of 10 volts. As the pulse is generated, the voltage in circuit branch 404 and 406 increases. At some point, the voltage reaches a value that will reverse bias diode $D_1$. When diode $D_1$ is reverse biased, it acts as an open circuit and current flowing across the diode $D_1$ stops. If the drive signal on transducer element 208 is bipolar, both diode $D_1$ and diode $D_2$ may be reverse biased for certain parts of the drive signal. FIG. 6 shows the exemplary embodiment of FIG. 2 in the case where the transmit/receive switch 206 is reverse biased. In FIG. 6, the transmission signal 203 can still reach transducer element 208, but receive assembly 204 is isolated from the high voltage drive pulse as illustrated as an opening 602 in the connection between the transmit assembly 202 and the receive assembly 204.

Note that the exemplary transmit receive switch shown in FIG. 4 implements protection against excessive voltage being seen at the receiver assembly using a minimal number of components that are fairly compact in size. The circuit of FIG. 4 is exemplary only and modifications can be made within the scope of the present invention.

Figure 7:
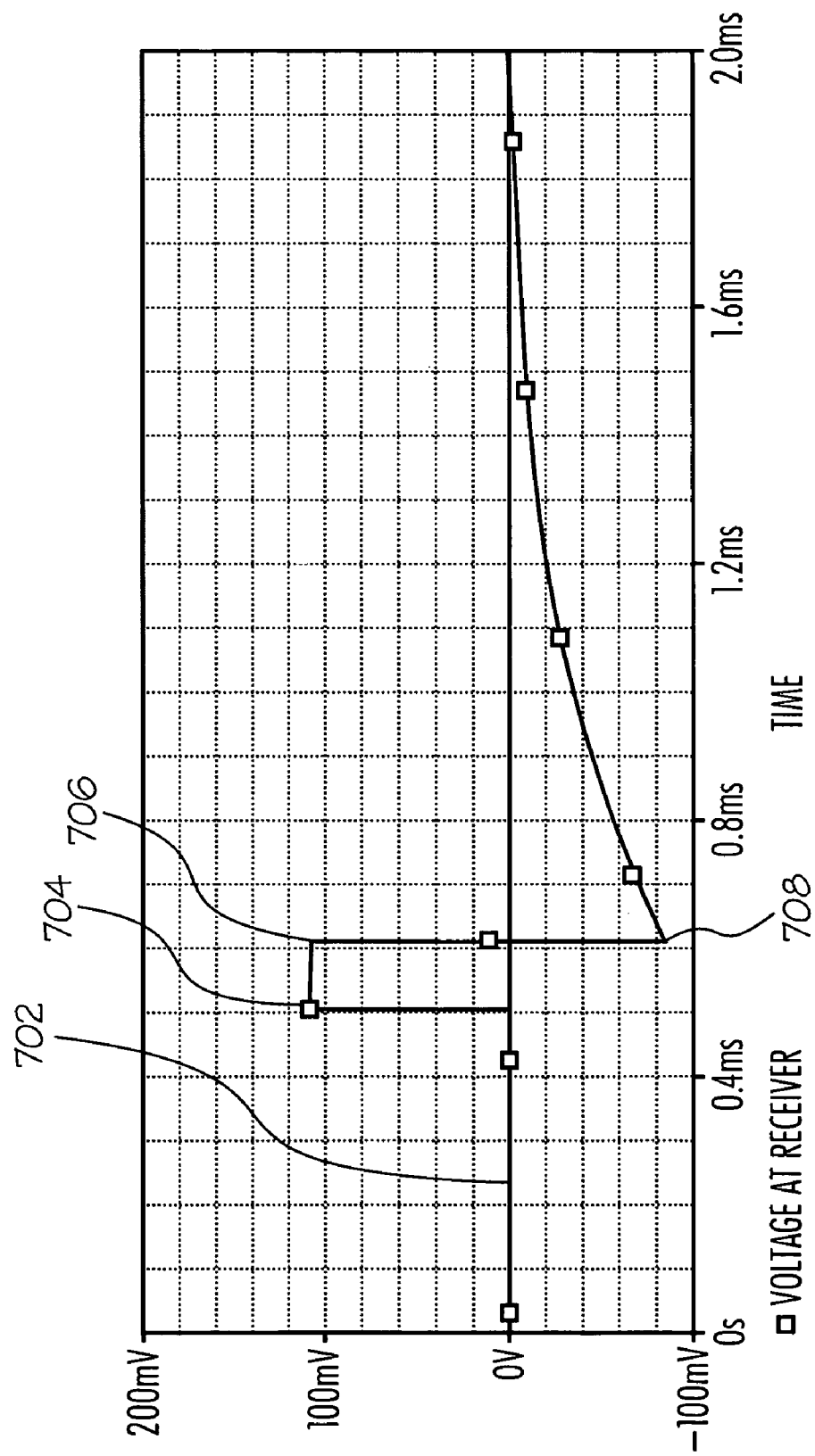
FIG. 7 is a graph of the voltage seen by the receiver electronics with a 50 ohm input impedance, when the drive pulse on the exemplary ultrasonic transducer is 10 volts.

FIG. 7 illustrates the voltage seen by a receiver with a 50 ohm input impedance during a drive signal of, in this example, 10 volts. As seen in FIG. 7, a voltage plot 702 of the voltage at the receiver reaches a peak, labeled as a first point 704, of approximately 100 mv. This 100 mv represents the voltage needed to overcome the bias potential set by the voltage source, the resistors and the resistance of the diode.

Also, in FIG. 7, for duration of an additional 1 ms past point 704, where the 1 ms corresponding to the length of the drive signal, the voltage seen at the receiver assembly 204 experiences a small drop in voltage from point 704 to point 706. After 1 ms, when the drive pulse ends, the voltage seen at the receiver drops to a negative value, point 708, thereafter it returns to the baseline voltage of 0 volts. This relaxation behavior is due to the filtering nature of the R-C networks and other components used in the circuit. The amount of this negative overshoot can be altered by adjusting the component values in the circuit but it is also important that certain frequency response goals are met to ensure that the sensed signal are within the pass band of the circuit. Varying the type of components (such as between resistors, capacitors and inductors), and the arrangement of components, will also vary the shape of the voltage plot. Most salient is the fact that high voltage drive signals will be blocked from the receiver.

Figure 8:
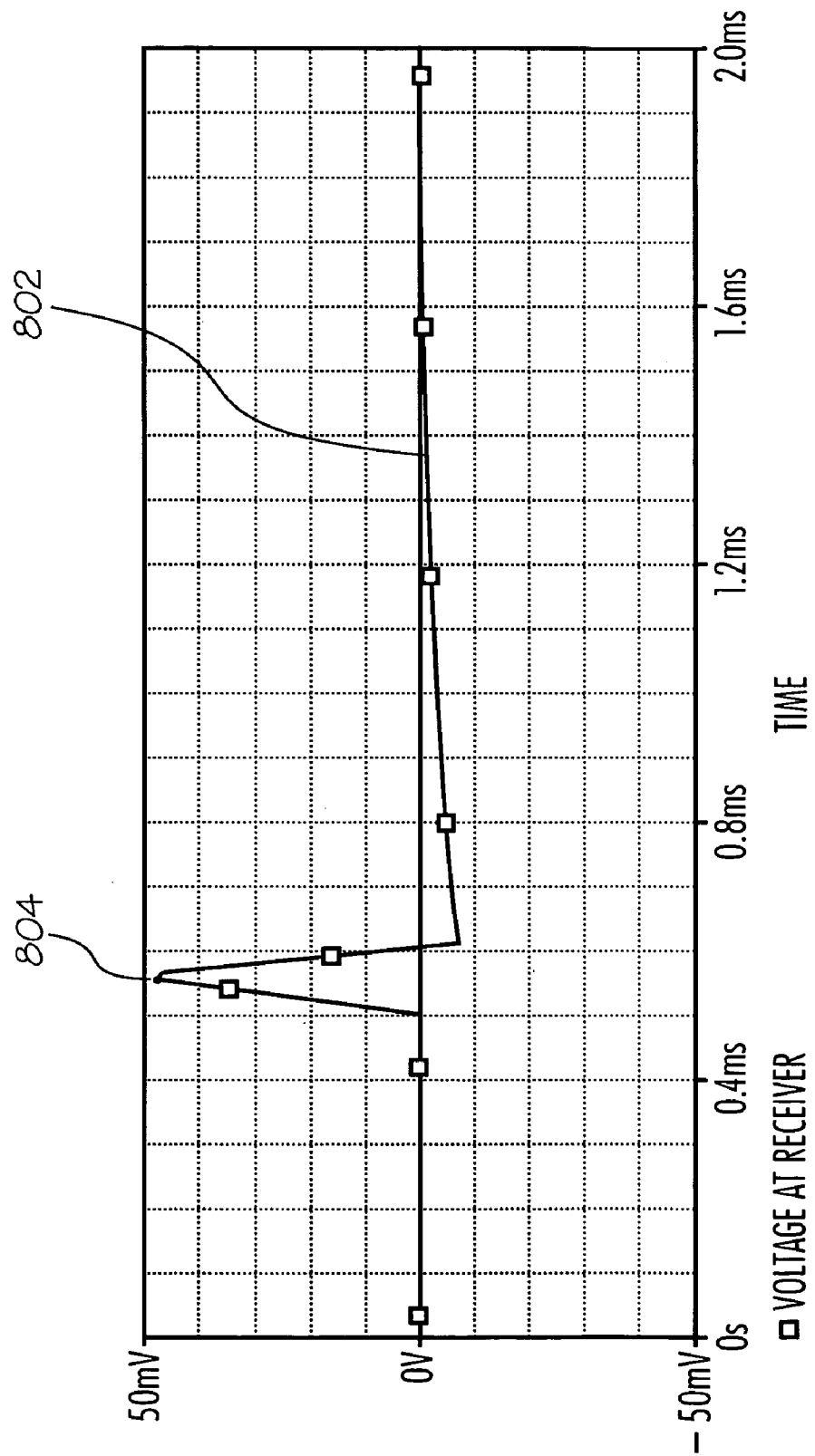
FIG. 8 is a graph of the voltage seen by the receiver electronics with a 50 ohm input impedance when a 100 mV voltage spike is generated by the exemplary ultrasonic transducer operating as a receiver sensing elastic waves.

FIG. 8 is a graph illustrating the voltage received at 50 ohm input impedance receiver when the drive pulse is not large enough to reverse bias the diode $D_1$. This graph illustrates a voltage plot 802 of the voltage at the receiver when the drive voltage is 100 mv. As seen in FIG. 8, the maximum voltage 804 seen at the receiver is approximately 50 mv, which is roughly half the drive voltage. In this example, since a large voltage pulse is not present, the transmit/receive switch is not in the open position.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

The invention claimed is:

1. A transducer for use in a structural health monitoring system, comprising:
 a transducer element including a first side and a second side and configured to be coupled to a test structure;
 a transmit assembly including a voltage driver coupled to the first side and the second side of the transducer element, the voltage driver configured to produce a drive signal to the first side and an inverse of the drive signal to the second side;

a receive assembly coupled to the transducer element, the receive assembly configured to receive mechanical pulses from the test structure; and a transmit/receive switch coupled to the receive assembly and the transmit assembly, the transmit/receive switch open when the transmit assembly is providing the drive signal.

2. The transducer of claim 1 wherein the transmit/receive switch comprises at least one diode that is reverse biased when the drive pulse exceeds a reverse bias threshold.

3. The transducer of claim 2 further comprises a voltage source coupled to the at least one diode, the voltage source configured to forward bias the at least one diode.

4. The transducer of claim 1 wherein the transducer element is a piezoelectric element.

5. The transducer of claim 4 wherein the piezoelectric element is a piezoelectric ceramic.

6. The transducer of claim 1 wherein the transducer element is configured to produce Lamb waves in the test structure.

7. The transducer of claim 1 wherein the voltage driver is configured to provide a multi-cycle square wave drive signal to the first side of the transducer element and an inverted multi-cycle square wave drive signal to the second side of the transducer element.

8. The transducer of claim 7 wherein the voltage driver comprises an inverter to invert the multi-cycle square wave drive signal to form the inverted multi-cycle square wave drive signal provided to the second side of the transducer element.

9. The transducer of claim 1 wherein the transmit assembly produces a 10 v square wave.

10. The transducer of claim 1 wherein the test structure is an aircraft skin.

11. A structural health monitoring system for use as an imbedded monitoring system comprising:

a transducer element including a first side and a second side and configured to be coupled to a test material;

a transmit assembly including a voltage driver coupled to the first side and the second side of the transducer element, the voltage driver configured to produce a drive pulse to the first side and an inverse of the drive pulse to the second side;

a receive assembly coupled to the transducer element, the receive assembly configured to receive mechanical pulses from the test material and generate characteristic data relating to the test material in response thereto;

a transmit/receive switch coupled between the receive assembly and the transmit assembly, the transmit/receive switch open when the transmit assembly is providing the drive pulse; and a processor coupled to the receive assembly, the processor configured to evaluate the characteristic data generated by the receive assembly.

12. The system of claim 11 wherein the transmit/receive switch comprises a diode that becomes reverse biased and acts as an open circuit when the drive pulse exceeds a reverse bias threshold.

13. The system of claim 12 further comprising a voltage source coupled to the at least one diode, the voltage source configured to forward bias the at least one diode.

14. The system of claim 11 wherein the transducer element is a piezoelectric element.

15. The system of claim 14 wherein the piezoelectric element is a piezoelectric ceramic.

16. The system of claim 11 wherein the transducer element is configured to produce lamb waves in the test material.

17. The system of claim 11 wherein the transmit assembly further comprises a pulse generator coupled to the first side of the transducer element and the second side of the transducer element, the pulse generator comprising:

a signal source configured to generate a voltage waveform; and a voltage driver coupled to the signal source, the voltage driver configured to present an inverse of the voltage waveform to the first side of the transducer element and the waveform to the second side of the transducer element.

18. The system of claim 17 wherein the processor is configured to activate the voltage driver to initiate a pulse.

19. The system of claim 11 wherein the transmit assembly produces a 10 v square wave.

20. The system of claim 11 wherein the test material is an aircraft skin.

21. A transducer having a single transducer element for use in a structural health monitoring system permanently mounted to a test material, the transducer comprising:

a transmit assembly coupled to the single transducer element, the transmit assembly comprising:

a voltage driver coupled to a first side of the transducer element and a second side of the transducer element, the voltage driver configured to provide a drive pulse comprising an alternate voltage to the first side of the transducer element and then to the second side of the transducer element;

a receive assembly coupled to the single transducer element, the receive assembly configured to receive mechanical pulses from the test material; and a transmit/receive switch coupled to the receive assembly and the transmit assembly, the transmit/receive switch open when the transmit assembly is providing a drive pulse.

22. The transducer of claim 21 wherein the transmit/receive switch comprises at least one diode that is reverse biased when the drive pulse exceeds a reverse bias threshold.

23. The transducer of claim 22 further comprises a voltage source coupled to the at least one diode, the voltage source configured to forward bias the at least one diode.

24. The transducer of claim 21 wherein the transducer element is configured to produce and detect lamb waves in the test material.

25. The transducer of claim 21 wherein the voltage driver further comprises an inverter configured to invert a voltage wave to form an inverted voltage waveform, the inverted voltage waveform provided to a first side of the transducer element and wherein an uninverted voltage waveform is provided to the second side of the transducer element.

26. The transducer of claim 1 wherein the transducer structural health monitoring system is coupled to an aircraft skin.

* * * * *